(12) United States Patent
Bornzin et al.

(10) Patent No.: US 7,653,440 B1
(45) Date of Patent: Jan. 26, 2010

(54) STIMULATION LEAD AND METHODS OF STIMULATING

(75) Inventors: Gene A. Bornzin, Simi Valley, CA (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 609 days.

(21) Appl. No.: 11/172,755

(22) Filed: Jun. 30, 2005

(51) Int. Cl.
*A61N 1/00* (2006.01)

(52) U.S. Cl. ..................................... 607/116
(58) Field of Classification Search ................. 607/14, 607/17, 37, 116, 9, 42
See application file for complete search history.

(56) References Cited

U.S. PATENT DOCUMENTS

| | | | |
|---|---|---|---|
| 4,712,555 A | 12/1987 | Thornander et al. ... | 128/419 PG |
| 4,788,980 A | 12/1988 | Mann et al. ........... | 128/419 PG |
| 4,940,052 A | 7/1990 | Mann et al. ........... | 128/419 PG |
| 5,243,980 A | 9/1993 | Mehra ............................ | 607/6 |
| 5,334,221 A | 8/1994 | Bardy ......................... | 607/14 |
| 5,356,425 A | 10/1994 | Bardy et al. ................. | 607/14 |
| 5,411,531 A | 5/1995 | Hill et al. ..................... | 607/14 |
| 5,466,254 A | 11/1995 | Helland ...................... | 607/123 |
| 5,476,483 A | 12/1995 | Bornzin et al. ................ | 607/17 |
| 5,507,784 A | 4/1996 | Hill et al. ...................... | 607/14 |
| 6,266,564 B1 * | 7/2001 | Hill et al. ........................ | 607/9 |
| 6,314,323 B1 | 11/2001 | Ekwall ......................... | 607/23 |
| 2006/0206159 A1 * | 9/2006 | Moffitt et al. ................. | 607/37 |

OTHER PUBLICATIONS

Carlson, Mark D. MD, Ma et al., "*Selective Stimulation of Parasympathetic Nerve Fibers to the Human Sinoatrial Node*," Circulation 1992;85:1311-1317.
Du, Xiao-Jun et al., "*Response to Cardiac Sympathetic Activation in Transgenic Mice Overexpressing $\beta_2$-Adrenergic Receptor*," The Amer Phys Soc 1996; H630-H636.
Murakami, Masahiko M.D. et al., "*Effects of Cardiac Sympathetic Nerve Stimulation on the Ventricular End-Systolic Pressure-Volume Relationship and Plasma Norepinephrine Dynamics in Dogs*," Jpn Circ J 1997; 61:864-871.
Pauza, Dainius H. et al., "*Morphology, Distribution, and Variability of the Epicardiac Neural Ganlionated Subplexes in the Human Heart*," The Anatomical Record, 259:353-382 (2000).

* cited by examiner

*Primary Examiner*—George Manuel

(57) ABSTRACT

An exemplary method includes passing a lead through a wall of an epicardial vein, an epicardial venous structure and/or a cardiac chamber wherein the lead includes an electrode portion; positioning the electrode portion proximate to an autonomic nerve and/or other tissue region; and delivering an electrical signal to the electrode portion to stimulate the autonomic nerve and/or other tissue region and thereby change cardiac function.

9 Claims, 13 Drawing Sheets

METHOD FOR STIMULATING AUTONOMIC NERVES

STIMULATION LEAD AND METHODS OF STIMULATING

TECHNICAL FIELD

Subject matter presented herein generally relates to cardiac pacing or stimulation therapy.

BACKGROUND

So called "fat pads" exist on the epicardial surface and are regions often associated with autonomous activity. Various patents discuss stimulation of fat pads to affect the heart. For example, U.S. Pat. No. 5,507,784, entitled "Method and apparatus for control of A-V interval," to Hill and Mehra, issued Apr. 16, 1999 ('784 patent), discusses stimulation of fat pads associated with the SA and AV nodes. In particular, the '784 patent states that the "fat pad associated with the SA node . . . is located along the anterior AV groove in most humans" and that the "fat pad associated with the AV node . . . is located along the posterior AV groove in most humans." U.S. Pat. No. 6,266,564, entitled "Method and device for electronically controlling the beating of a heart," to Hill and Jonkman, issued Jul. 24, 2001 ('564 patent), also discusses "fat pad" stimulation. In particular, the '564 patent references a study entitled "Selective Stimulation of Parasympathetic Nerve Fibers to the Human Sinoatrial Node," Circulation, 85(4): 1311-1317 (1992), which reported that "cardiac parasympathetic nerve fibers located in an epicardial fat pad at the margin of the right atrium, the superior vena cava, and the right pulmonary vein in humans could be electrically stimulated to affect the heart rate." However, as discussed herein, a more recent study by Pauza et al., "Morphology, distribution, and variability of the epicardiac neural ganglionated subplexuses in the human heart," The Anatomical Record 259(4): 353-382 (2000), demonstrates that significant populations of autonomic nerves exist in other epicardial locations.

The aforementioned '784 patent also discusses a lead to stimulate the AV nodal "fat pad" wherein the lead has two electrodes located within the coronary sinus, adjacent the ostium. Further the '784 patent states that "AV nodal fat pad stimulation may also be accomplished by means of one electrode located adjacent the ostium of the coronary sinus and a second electrode located in the inferior vena cava, by means of electrodes located in the left atrium or by means of epicardial electrodes applied on or adjacent the AV nodal fat pad." However, the '784 patent does not disclose any epicardial electrodes or leads having epicardial electrodes. While the aforementioned '564 patent discusses electrodes for stimulation of "fat pads," such stimulation is limited to electrodes located on transvenous leads located in veins adjacent nerve fibers to be stimulated. Given the relationship between fat pad stimulation and cardiac function, a need exists for alternative or improved stimulation techniques. In particular, a need exists for epicardially positionable leads that can stimulate a variety of autonomic nerves or other cardiac tissue.

SUMMARY

Exemplary methods, devices, systems, etc., for stimulating autonomic nerves and/or other cardiac tissue are disclosed. An exemplary method for stimulating tissue includes: passing a lead through a wall of an epicardial vein and/or an epicardial venous structure wherein the lead includes an electrode portion; positioning the electrode portion proximate to (including in contact with) an epicardial autonomic nerve and/or other cardiac tissue; and delivering an electrical signal to the electrode portion to stimulate the epicardial autonomic nerve and/or the other cardiac tissue and thereby change cardiac operation. The exemplary method further optionally includes use of a deployable electrode portion. According to various exemplary methods, positioning includes positioning an electrode portion proximate to an epicardial autonomic nerve in a subplexus. Such subplexuses include, but are not limited to, a dorsal right atrial ganglionated subplexus, a ventral right atrial ganglionated subplexus, a middle dorsal ganglionated subplexus, a left dorsal ganglionated subplexus.

Another exemplary method includes positioning an electrode portion proximate to (or in) an epicardial fat pad wherein delivery of an electrical signal to the fat pad via the electrode portion results in a change in cardiac function. For example, according to such a method, the delivery of an electrical signal may stimulate an autonomic nerve located in and/or proximate to the fat pad that is associated with the heart's AV node and/or SA node. Of course, such an electrode may optionally stimulate other cardiac tissue.

An exemplary device includes a lead having an electrode portion wherein the electrode portion is passable through a wall of a vein, a venous structure, and/or a cardiac chamber and positionable epicardially proximate to a tissue region.

Various exemplary devices, systems, methods, etc., described herein, and equivalents thereof, are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are generally used to reference like parts or elements.

Exemplary Stimulation Device

The techniques described below are intended to be implemented in connection with any stimulation device that is configured or configurable to stimulate nerves and/or stimulate and/or shock a patient's heart.

Figure 1:
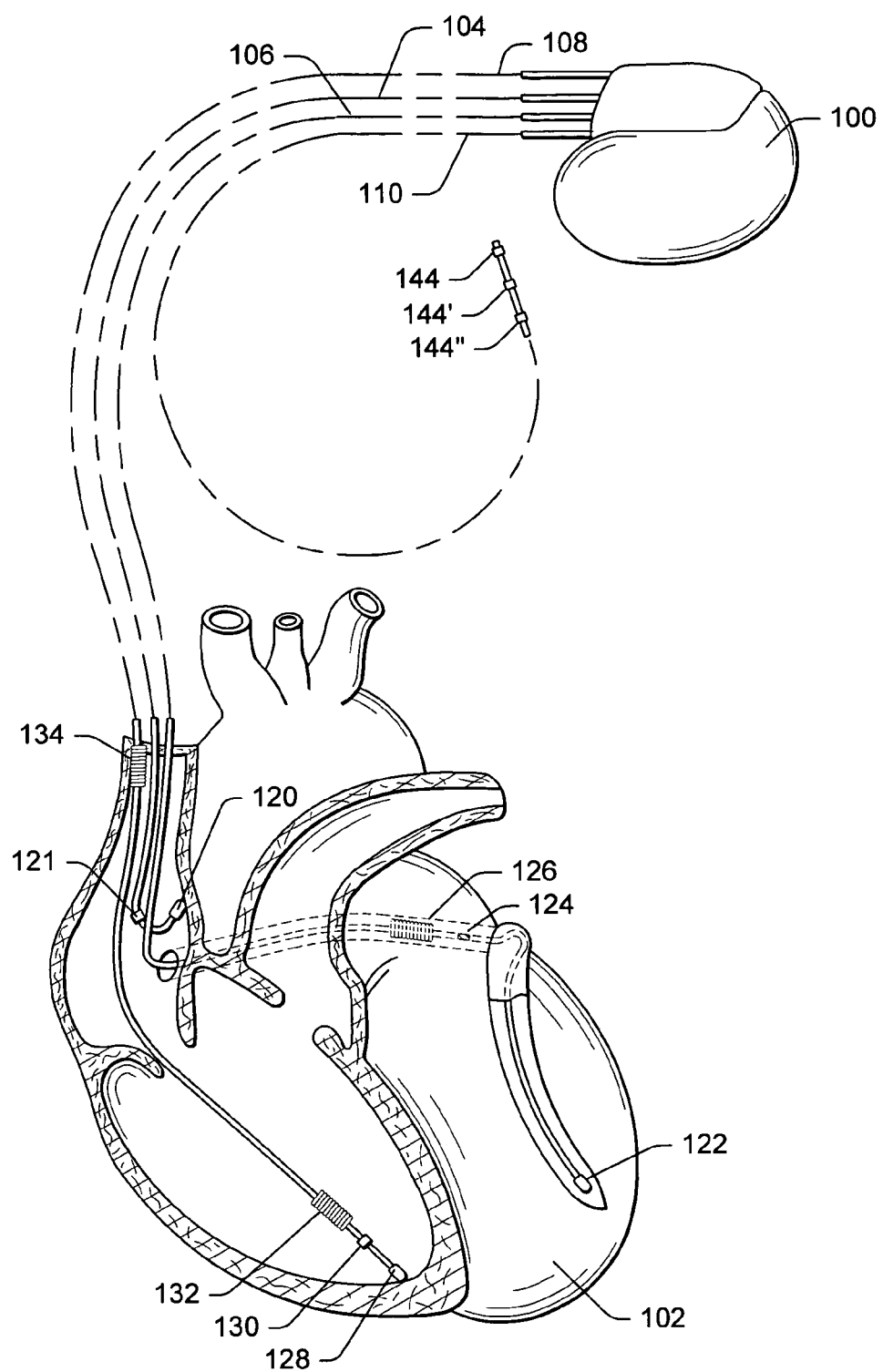
FIG. 1 is a simplified diagram illustrating an exemplary implantable stimulation device in electrical communication with at least three leads implanted into a patient's heart and at least one other lead for delivering stimulation and/or shock therapy. Devices having fewer or more leads may also be suitable.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the exemplary device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. As described herein, a stimulation device may have fewer, the same or more leads than the exemplary device 100. Various exemplary leads or lead portions described herein are optionally used with a stimulation device such as, for example, the device 100.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for epicardial positioning and/or stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for epicardial positioning and/or stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in the example of FIG. 1, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead. In addition, an exemplary right ventricular lead may also include at least one electrode positionable epicardially proximate to a tissue region.

Figure 2:
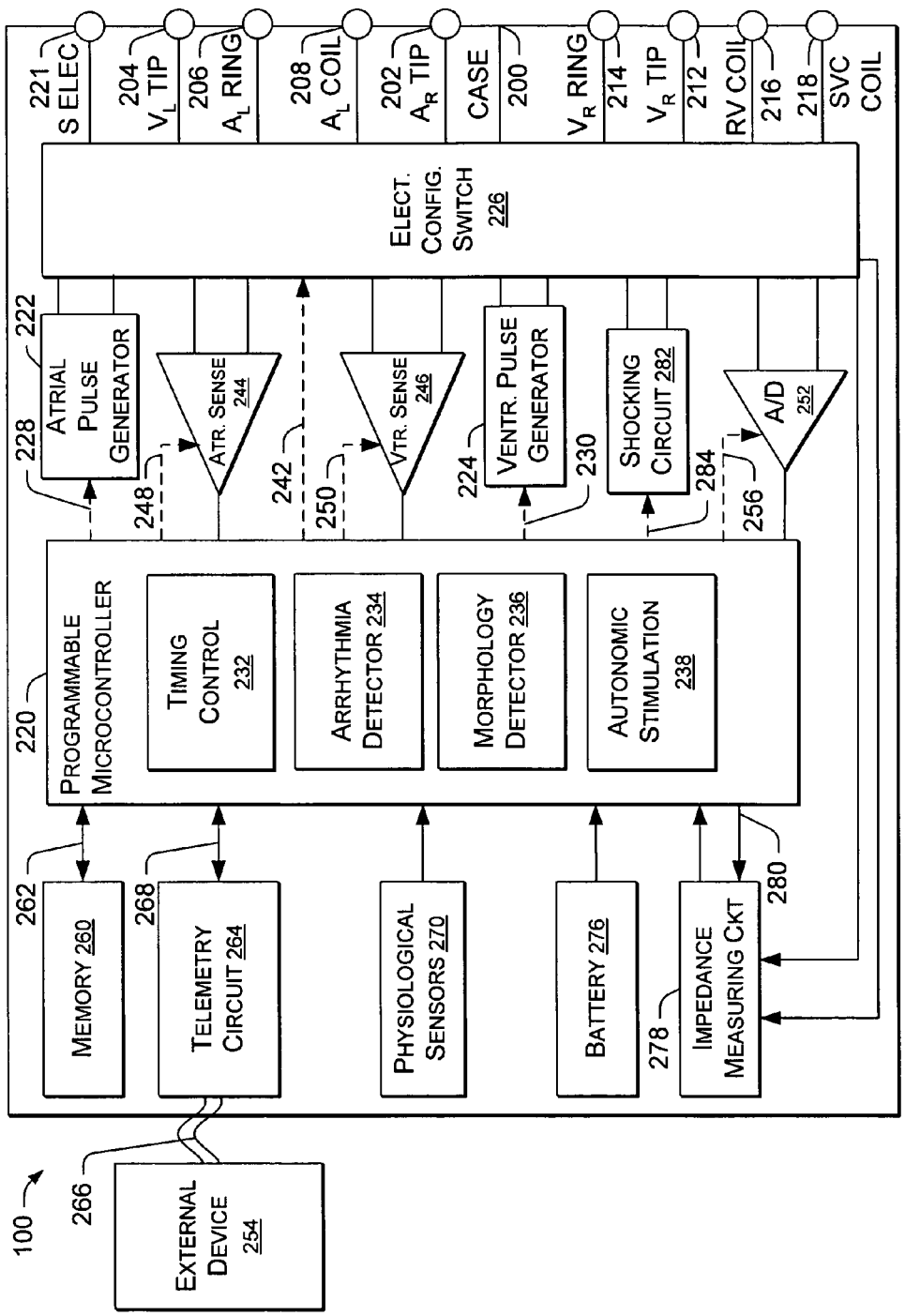
FIG. 2 is a functional block diagram of an exemplary implantable stimulation device illustrating basic elements that are configured to provide cardioversion, defibrillation, pacing stimulation and/or autonomic nerve stimulation. The implantable stimulation device is further configured to sense information and administer stimulation pulses responsive to such information.

FIG. 2 shows an exemplary, simplified block diagram depicting various components of the stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, various techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 may act as an electrode for nerve or other stimulation. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy to effect operation of any or all of the four chambers of the heart the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses. The pulse generators 222 and 224 may also generate pulses suitable for stimulation of autonomic nerves.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an autonomic nerve stimulation module 238 for performing a variety of tasks related to autonomic nerve stimulation. This component can be utilized by the stimulation device 100 for determining desirable times to administer various therapies, including, but not limited to, sympathetic stimulation to, for example, increase contractility or rate of a patient's heart and/or parasympathetic stimulation to, for example, decrease rate of a patient's heart. The autonomic module 238 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied, as appropriate, to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. The implantable device 100 optionally includes an ability to sense information and store a relatively large amount of such information (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to about 0.5 J), moderate (e.g., about 0.5 J to about 10 J), or high energy (e.g., about 11 J to about 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of about 5 J to about 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Overview

Various exemplary methods, leads, systems, etc., described herein are suitable for stimulating cardiac tissue. For example, an exemplary lead includes electrodes suitable for positioning epicardially proximate to a tissue region. Once positioned, electrical pulses, delivered via the lead and electrodes, may stimulate autonomic nerves and/or other cardiac tissue. Of course, positioning and/or pulse characteristics may determine whether a pulse stimulates an autonomic nerve or other cardiac tissue. According to various exemplary methods and/or exemplary leads, epicardial positioning is typically achieved via a transvenous route.

Autonomic Nervous System

The autonomic nervous system includes sympathetic and parasympathetic pathways. Both pathways include afferent pathways (e.g., from an organ to central neurons) and efferent pathways (e.g., postganglionic neurons from ganglia to an organ) that relate to functioning of the heart. For example, parasympathetic efferent postganglionic neurons, when stimulated, suppress atrial rate and contractile force, atrioventricular nodal conduction, and ventricular contractile force, also known as contractility or inotropy. Sympathetic efferent postganglionic neurons, when stimulated, generally increase heart rate and increase contractility. Note that contractility is associated with the term "inotropy", heart rate is associated with the term "chronotropy" and conduction velocity is associated with the term "dromotropy."

Stimulation of parasympathetic nerves acts to decrease heart rate while stimulation of sympathetic nerves acts to increase heart rate. Regarding sympathetic stimulation, norepinephrine is released by sympathetic nerves. After its release, norepinephrine acts on the sinoatrial node (SA node) to increase the rate of diastolic depolarization, and thereby increase heart rate, and acts on the atrioventricular node (AV node) to increase the velocity of conduction and diminish the refractory period during which the AV node is unresponsive to stimuli coming from the atrium.

Contractility (or inotropy) refers to the force or strength of cardiac muscle contractions. Stimulation of sympathetic nerves causes active contractility whereas Frank-Starling mechanism causes passive contractility. Active contractility involves norepinephrine, which increases myocardial calcium permeability (or conductance) and hence actin/myosin crossbridge interactions. Other mechanisms may also accompany the increase in calcium permeability. In general, an increase in ventricular contractility causes an increase stroke volume, which, in turn, can increase cardiac output.

Changes in inotropic state are particularly important during exercise. Increases in inotropic state helps to maintain stroke volume at high heart rates. Increased heart rate alone decreases stroke volume because of reduced time for diastolic filling (decreased end-diastolic volume). When inotropic state increases at the same time, this decreases end-systolic volume to maintain stroke volume.

Figure 3:
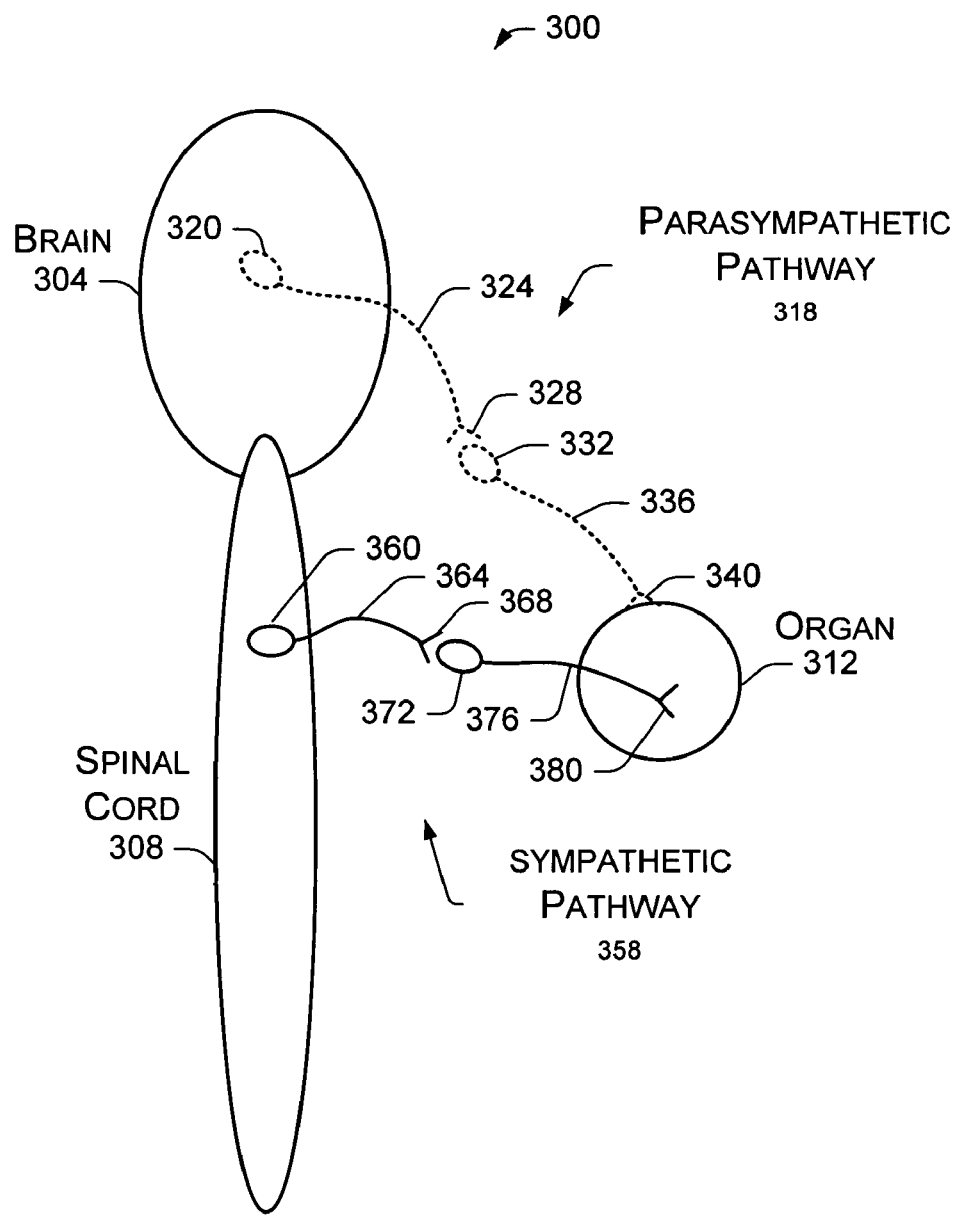
FIG. 3 is a simplified approximate anatomical diagram of a parasympathetic pathway and a sympathetic pathway of the autonomic nervous system.

As already mentioned, the autonomic nervous system includes parasympathetic and sympathetic pathways. Referring to FIG. 3, a simplified diagram of the autonomic nervous system 300 is shown. The system 300 illustrated includes a brain 304, a spinal cord 308, an organ 312, a parasympathetic efferent pathway 318 and a sympathetic efferent pathway 358. The parasympathetic efferent pathway 318 includes a preganglionic cell body 320 located in the brain 304, a preganglionic axon 324, a synaptic cleft 328, a postganglionic cell body 332, a postganglionic axon 336, and a postganglionic synaptic cleft 340 proximate to the organ 312. An exemplary parasympathetic stimulus originates at the brain 304 and ends at the postganglionic synaptic cleft 340 wherein a chemical is emitted to effect cell of the organ 312. A synaptic cleft may also be referred to as a neuroeffector junction. The sympathetic efferent pathway 358 includes a preganglionic cell body 360 located in the spinal cord 308, a preganglionic axon 364, a synaptic cleft 368, a postganglionic cell body 372, a postganglionic axon 376, and a postganglionic synaptic cleft 380 proximate to the organ 312. An exemplary sympathetic stimulus originates at the spinal cord 308 and ends at the postganglionic synaptic cleft 380 wherein a chemical is emitted to effect cell of the organ 312. In both pathways 318, 358, acetylcholine operates as a neurotransmitter to activate postganglionic neurons, i.e., preganglionic neurons are cholinergic. In parasympathetic pathways (e.g., the parasympathetic pathway 318), postganglionic neurons emit acetylcholine and are therefore cholinergic. However, in many sympathetic pathways (e.g., the sympathetic pathway 358), postganglionic neurons emit norepinephrine and are therefore adrenergic. While FIG. 3 shows a one to one ratio of preganglionic to postganglionic neurons, note that a preganglionic neuron generally links to more than one postganglionic neuron, for example, in a sympathetic pathway, a preganglionic neuron to postganglionic neuron ratio may be approximately 1:32.

Pauza et al., "Morphology, distribution, and variability of the epicardiac neural ganglionated subplexuses in the human heart," The Anatomical Record 259(4): 353-382 (2000), reported that the epicardial plexus forms seven subplexuses: (I) left coronary or LC, (II) right coronary or RC, (III) ventral right atrial or VRA, (IV) ventral left atrial or VLA, (V) left dorsal or LD, (VI) middle dorsal or MD, and (VII) dorsal right atrial or DRA. Pauza et al., state that, in general, the human right atrium is innervated by two subplexuses (III, VII), the left atrium by three subplexuses (IV, V, VI), the right ventricle by one subplexus (II), and the left ventricle by three subplexuses (I, V, VI). Pauza et al., also suggested that "left epicardial subplexuses (e.g., I, IV, V, VI) may be considered as being formed by nerves derived from the left side of the deep extrinsic cardiac plexus, whereas ventral and dorsal right atrial subplexuses (III, VII) should be considered as being supplied by preganglionated nerves extending from the right vagus nerve and right sympathetic trunk, as their branches course in the adventitia of the right pulmonary artery and superior vena cava." Further, according to Pauza et al., the left coronary (I), right coronary (II), ventral left atrial (IV) and middle dorsal (VI) subplexuses "may be considered as being formed by the deep extrinsic plexus that receives equally from both vagi and sympathetic trunks." Note that in the Pauza et al., reference, the terms "epicardiac preganglionated nerves" and "epicardiac postganglionated nerves" are differentiated from the meanings of "axons of the preganglionic and postganglionic neurons" that are valid in the nomenclature of the autonomic nervous system, for example, as referred to above with reference to FIG. 3. Thus, the term "postganglionic neurons" includes epicardiac/epicardial preganglionic neurons as well as epicardiac/epicardial postganglionic neurons.

Pauza et al., also states that "the human SA-node is supplied by abundant postganglionic nerves deriving both from the VRA (III) and DRA (VII) subplexuses, whereas nerves spreading to the region of the human AV-node originated from the MD (VI) subplexus in the main and from the LD (V) subplexus in part." Regarding the VRA (III) subplexus, Pauza et al., state that "preGNs [pre-ganglionated nerves] of this subplexus [VRA (III)] entered the epicardium at the superior interatrial sulcus, where a large epicardial fat pad was consistently located nearby the HH [heart hilum]" and that the ganglionated field of the VRA (III) subplexus usually had the largest number and highest density of epicardial ganglia in a ventral region along the root of the superior vena cava. Regarding the DRA (VII) subplexus, Pauza et al., state that the largest number and density of ganglia were located in the dorsal superior right atrial region and root of the superior vena cava region.

Regarding the MD (VI) subplexus, Pauza et al., state that the largest number of ganglia was located in a dorsal superior left atrial region. Regarding the LD (V) subplexus, Pauza et al., state that this subplexus accounted for about 30% of all subplexus ganglia and had a ganglionated field located in pre-left coronary sulcus, dorsal left coronary sulcus, and middle left atrial regions. In addition, post ganglionated nerves from this subplexus "extended obliquely or along the left dorsal coronary sulcus and nearby the crux cordis intervened into a complex neural meshwork that was also formed by the nerves of the middle dorsal subplexus [MD (VI)]." A "fat pad" is located at and/or near the location of this neural meshwork. Note that this "fat pad" is not considered one of the seven elaborated neural subplexuses.

Thus, stimulation of the VRA (III) and/or DRA (VII) subplexuses and/or nerves stemming from these subplexuses will allow for some degree of control over SA node operation. Similarly, stimulation of the MD (VI) and/or LD (V) subplexuses and/or nerves stemming from these subplexuses will allow for some degree of control over AV node operation. Note that possible stimulation sites are not limited to "fat pads" locations.

Upon stimulation, end terminals (or terminal knobs) of the postganglionic sympathetic nerves (e.g., epicardial postganglionic sympathetic nerves) release norepinephrine whereas parasympathetic nerves release acetylcholine. Both of these neuroeffectors act through receptors. Cardiac sympathetic receptors are mostly the beta-1 subtype. Beta-1 receptors, which respond approximately equally to norepinephrine and epinephrine, generally act on the myocardium to increase heart rate, contractility, and/or conduction velocity. Hence, by increasing the rate of depolarization and thereby decreasing the interval between SA node action potentials sympathetic neuroeffectors can increase heart rate. In contrast, parasympathetic cholinergic muscarinic receptors act on the sinoatrial (SA) node to decrease heart rate and act on the atrioventricular (AV) node to decrease conduction velocity. More specifically, acetylcholine hyperpolarizes the membrane potential of SA node cells and slows diastolic depolarization. In this manner, acetylcholine increases the interval between SA node action potentials and slows the heart rate.

Electrical stimulation of autonomic nerves has been reported in the literature, see, e.g., Murakami, et al., "Effects of cardiac sympathetic nerve stimulation on the left ventricular end-systolic pressure-volume relationship and plasma norepinephrine dynamics in dogs," Jpn. Circ. J. 61(10): 864-71 (1997); and Du, et al., "Response to cardiac sympathetic activation in transgenic mice overexpressing beta 2-adrenergic receptor." Am-J-Physiol. August; 271(2 Pt 2): H630-6 (1996).

According to various exemplary methods and/or devices described herein, a series of pulses, or a pulse train, is optionally delivered by an implantable stimulation device to stimulate an autonomic nerve. The pulse train optionally includes pulse parameters or pulse train parameters, such as, but not limited to, frequency, pulse duration (or pulse width), number of pulses, and/or amplitude. These parameters may have broad ranges and vary over time within any given pulse train. In general, a power level for individual pulses and/or pulse trains is determined based on these parameters and/or other parameters. Exemplary ranges for pulse frequency include frequencies ranging from approximately 0.2 to approximately 20 Hz, and, in particular, frequencies ranging from approximately 1 Hz to approximately 4 Hz. Exemplary ranges for pulse duration, or pulse width for an individual pulse (generally within a pulse train), include pulse widths ranging from approximately 0.01 milliseconds to approximately 5 milliseconds and, in particular, pulse widths ranging from approximately 0.1 milliseconds to approximately 1.6 milliseconds. Exemplary pulse amplitudes are typically given in terms of current or voltage; however, a pulse or a pulse trains may also be specified by power, charge and/or energy. For example, in terms of current, exemplary ranges for pulse amplitude include amplitudes ranging from approximately 0.02 mA to approximately 20 mA, in particular, ranging from 0.1 mA to approximately 5 mA. Exemplary ranges for pulse amplitude in terms of voltage include voltages ranging from approximately 2 V to approximately 50 V, in particular, ranging from approximately 4 V to approximately 15 V.

For pulses delivered by implantable stimulation devices having a fixed or otherwise limited power supply, i.e., a power supply having power limitations, average power of a pulse or a pulse train is usually limited acutely by the power capability of the power supply (e.g., battery, fuel cell, nuclear generator, etc.) and chronically by the capacity of the power supply and desired longevity of the device's usefulness. Average power of a pulse is generally given as peak power averaged over one cycle. For example, given a voltage of 10 V, a resistance of 1000 ohms, a pulse frequency of 20 Hz and a pulse width of 1 ms, the peak power is given as voltage squared divided by resistance, which is 0.1 W, and the average power is 20 Hz multiplied by 1 ms multiplied by 0.1 W, which is 0.002 W or 2 mW. The term "power", as used herein, includes, but is not limited to, peak power and average power.

Current drain is another factor often considered when determining power limitations of a power supply. Current drain is generally defined as the average amount of current drawn from a power supply in an implantable pulse generator in one hour. Current drain depends on many factors, including how frequently the device delivers pulses and at what parameters, the circuitry and/or the type of stimulation lead. Current drain is commonly expressed in millionths of an ampere or microamperes. A power drain based on current drain may be determined by the product of current drain and voltage. Such a power is optionally useful in determining a maximum power level for an autonomic stimulation pulse or pulses.

In general, a maximum power level or maximum power demand for an implantable device may be determined, in part, by the product of the voltage times the current capability of the battery (or other power supply) less circuit inefficiencies. Of course, desired power supply life (e.g., battery life) and/or other factors may be considered. For example, some implantable stimulation devices have a continuous power drain for one function (e.g., to drive a microchip, microprocessor or timing circuitry) and an intermittent function (e.g., such as pacing, measuring, signaling, etc.) which has intermittent power utilization. Consideration of such factors may be necessary in determining a tolerable and/or maximum power level and, in particular, in determining pulse parameters for autonomic nerve stimulation.

Epicardial Autonomic Pathways

According to various exemplary methods, devices, systems, etc., described herein, and equivalents thereof, stimulation of autonomic nerves allows for influence of cardiac activity. For example, various exemplary methods and corresponding stimulation devices rely on placement of a lead through a vein, a venous structure and/or a cardiac chamber. Suitable epicardial veins or venous structures include the inferior vena cava, the superior vena cava, the coronary sinus and veins that drain into the coronary sinus, either directly or indirectly. For example, the great cardiac vein passes along the interventricular sulcus, with the anterior interventricular coronary artery, and empties anteriorly into the coronary sinus; and the middle cardiac vein travels with the posterior (right) interventricular coronary artery and empties into the coronary sinus posteriorly. Other suitable veins include those that drain into the right atrium or right auricle. For example, the anterior cardiac vein passes through the wall of the right atrium and empties into the right atrium. In addition, a lead may pass through the wall of a cardiac chamber (e.g., right atrium, left atrium, right ventricle, or left ventricle).

Figure 4:
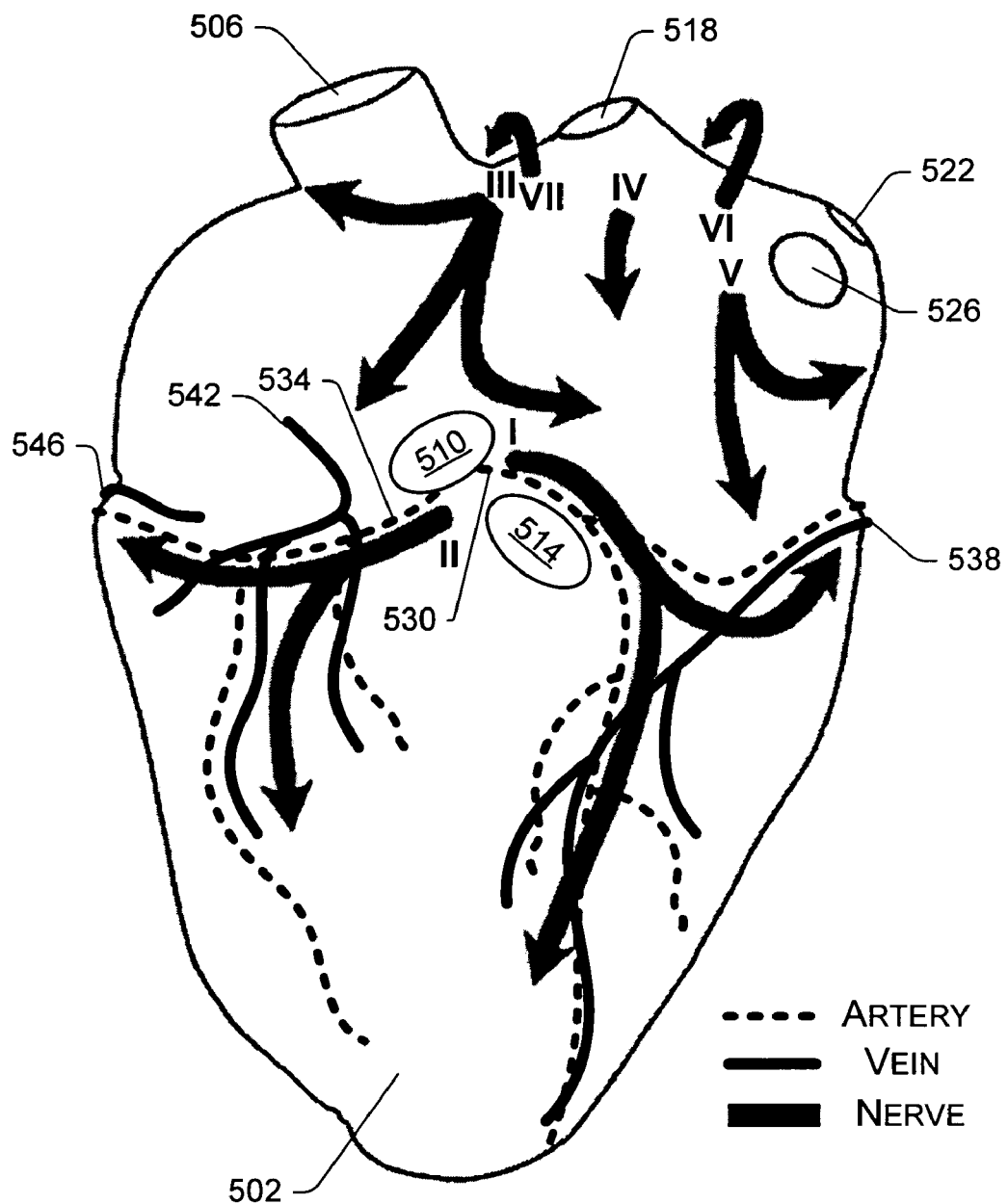
FIG. 4 is an approximate anatomical ventral view diagram of a human heart including some arteries, veins and nerves.

Referring to FIG. 4, a ventral diagram of a human heart 502 is shown. Various anatomical features of the heart 502 are also shown and include an opening to the superior vena cava 506, an opening to the aorta 510, an opening to the pulmonary trunk 514, an opening to the right superior pulmonary vein 518, an opening to the left inferior pulmonary vein 522, and an opening to the left superior pulmonary vein 526. FIG. 4 also shows some of the epicardial arteries (thick dashed lines) and veins (thick solid lines). Under normal conditions, epicardial arteries carry oxygenated blood to the myocardium, primarily myocardium of the ventricles while epicardial veins carry blood deoxygenated by the myocardium to the right atrium of heart 502. Pressure in the veins is generally, on average, much less than pressure in the arteries. For example, pressures in the coronary sinus generally do not exceed approximately 10 mm Hg.

Two major epicardial arterial networks are shown in FIG. 4 and associated with the left coronary artery 530 and the right coronary artery 534. The left coronary artery 530 stems from the aorta near the opening to the aorta 510 and travels along the base of the left ventricle where it branches. One branch of the left coronary artery travels on the epicardial surface of the left ventricle toward the apex of the heart 502 (known as the left anterior descending artery) while another branch travels on the epicardial surface of the left ventricle toward the dorsal side of the heart 502 (known as the circumflex branch of the left coronary artery). The right coronary artery 534 stems from the aorta near the opening to the aorta 510 and travels along the base of the right ventricle where it branches. Various branches of the right coronary artery 534 travel on the epicardial surface of the right ventricle while at least one branch travels on the epicardial surface of the right ventricle toward the dorsal side of the heart 502.

Three major epicardial venous networks are shown in FIG. 4, which are associated with the great cardiac vein 538, the anterior cardiac vein 542, and the small cardiac vein 546. The great cardiac vein 538 receives blood from a network that spreads across the ventral side of the epicardial surface of the left ventricle and major branches of the network extend toward the apex of the heart 502. As already mentioned, the great cardiac vein 538 travels on the epicardial surface near the base of the left ventricle to the dorsal side of the heart 502 where it joins the coronary sinus vein. The anterior cardiac vein 542 receives blood from a network that spreads across the ventral and dorsal sides of the epicardial surface of the right ventricle and major branches of the network extend toward the apex of the heart 502. As already mentioned, the anterior cardiac vein empties into the right atrium of the heart 502. The small cardiac vein 546 travels from the ventral epicardial surface to the dorsal epicardial surface where it empties into the coronary sinus.

FIG. 4 also shows the seven subplexuses as identified by Pauza et al. Preganglionate nerves enter the left coronary subplexus (I) and the right coronary subplexus (II) approximately between the opening to the aorta 510 and the opening to the pulmonary trunk 514. Preganglionate nerves enter the ventral right atrial subplexus (III) at the superior interatrial sulcus and non-regularly on the ventral surface of the root of the superior vena cava while preganglionated nerves enter the ventral left atrial subplexus (IV) approximately between the superior interatrial sulcus and left atrial nerve fold. Preganglionated nerves enter the left dorsal subplexus (V) approximately at the left atrial nerve fold and preganglionated nerves enter the middle dorsal subplexus (VI) approximately between the right and left superior pulmonary veins (see, e.g., 518, 526) and, non-regularly, between the right pulmonary veins and the inferior vena cava. Preganglionated nerves enter the dorsal right atrial subplexus (VII) approximately between the superior vena cava and the right superior pulmonary vein (see, e.g., 506, 518). As already mentioned, postganglionated nerves, and some preganglionated nerves, spread out from the subplexuses (I-VII) across the epicardial surface of the heart 502. The spreading of such nerves is shown by the thick solid arrows in FIG. 4 and FIG. 5, the latter of which shows a dorsal diagram of the heart 502.

Figure 5:
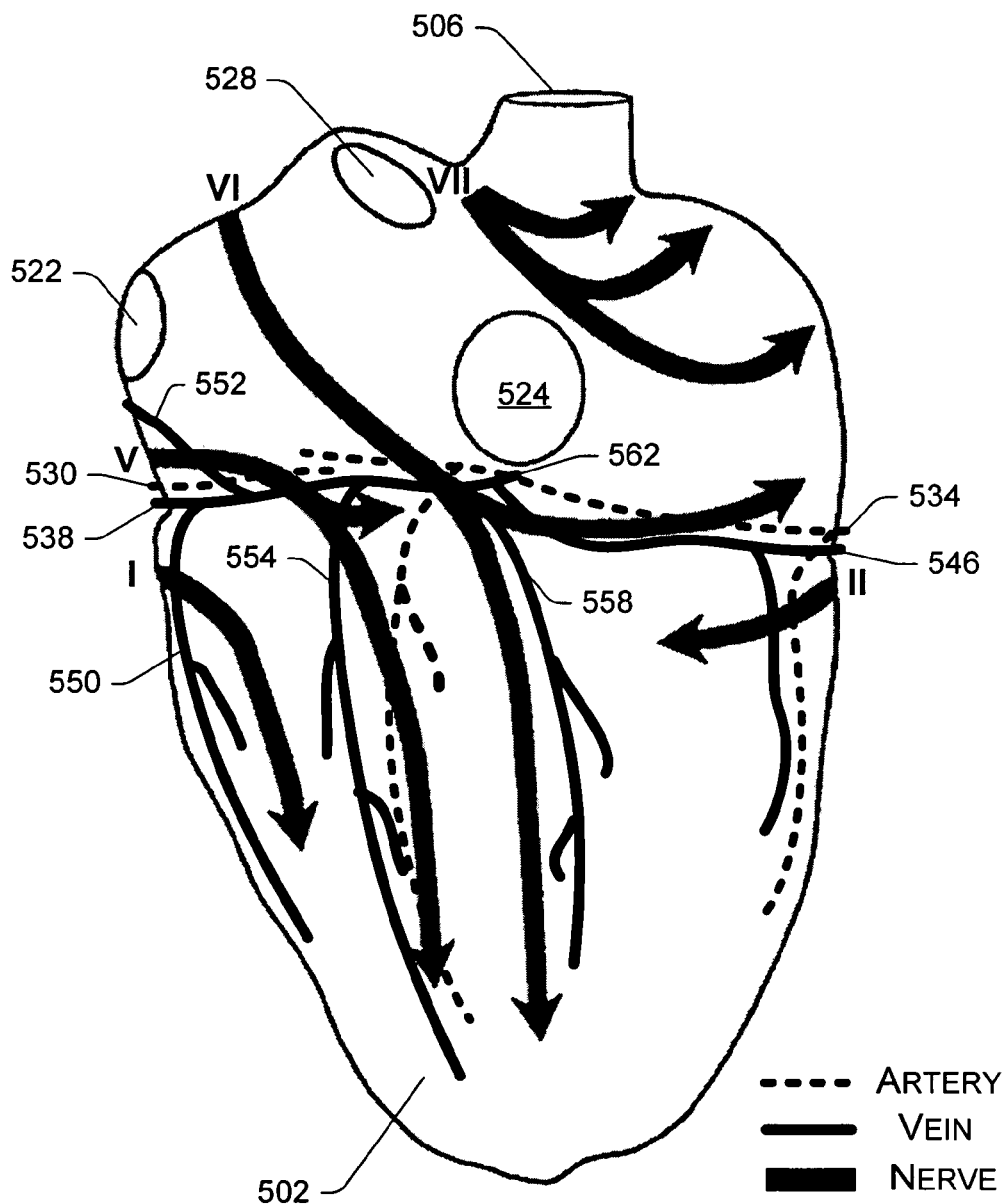
FIG. 5 is an approximate anatomical dorsal view diagram of a human heart including some arteries, veins and nerves.

Referring to FIG. 5, a dorsal diagram of the human heart 502 is shown. Various anatomical features of the heart 502 are also shown and include an opening to the superior vena cava 506, an opening to the inferior vena cava 524, an opening to the right inferior pulmonary vein 528, and an opening to the left inferior pulmonary vein 522. FIG. 5 also shows some of the epicardial arteries (thick dashed lines) and veins (thick solid lines). The arterial and venous networks shown on the dorsal epicardial surface of the heart 502 include extensions of networks from the ventral epicardial surface. For example, the dorsal epicardial surface includes networks stemming the right coronary artery 534 and the left coronary artery 530. In particular, the circumflex branch of the left coronary artery 530 is shown along with various extensions of the right coronary artery 534 one of which approaches the end of the circumflex branch. Venous epicardial structures shown in FIG. 5 include the coronary sinus 562, the great cardiac vein 538, the small cardiac vein 546, the oblique vein of the left atrium 552, the left marginal vein 550, the posterior vein of the left ventricle 554, and the middle cardiac vein 558. The aforementioned veins (538, 546, 550, 552, 554, 558) empty into the coronary sinus 562.

FIG. 5 also shows, via thick solid arrows, neural extensions of five of the subplexuses as identified by Pauza et al. Neural extensions of the left coronary subplexus (I) descend toward the apex of the heart 502 at and/or near the left marginal vein 550 and the posterior vein of the left ventricle 554. Neural extensions of the right coronary subplexus (II) traverse the heart 502 at and/or near the right coronary sulcus. Neural extensions of the left dorsal subplexus (V) descend toward the apex of the heart 502 at and/or near the posterior vein of the left ventricle 554 while neural extensions of the middle dorsal subplexus (VI) descend towards the apex of the heart 502 at and/or near the middle cardiac vein 558 and the small cardiac vein 546. Neural extensions of the dorsal right atrial subplexus (VII) extend around the right atrium at and/or near the superior vena cava (see, e.g., 506) and the inferior vena cava (see, e.g., 524).

As shown in FIGS. 4 and 5, various epicardial veins or venous structures travel at and/or near epicardial subplexuses and/or epicardial extensions of epicardial subplexuses. According to various exemplary methods and/or stimulation devices described herein, at least one lead passes through the wall of an epicardial vein, venous structure and/or cardiac chamber. Further, upon delivering a stimulus to at least one electrode on the lead, neural stimulation occurs, which preferably causes release of a neuroeffector, such as, but not limited to, acetylcholine and/or norepinephrine.

Figure 6:
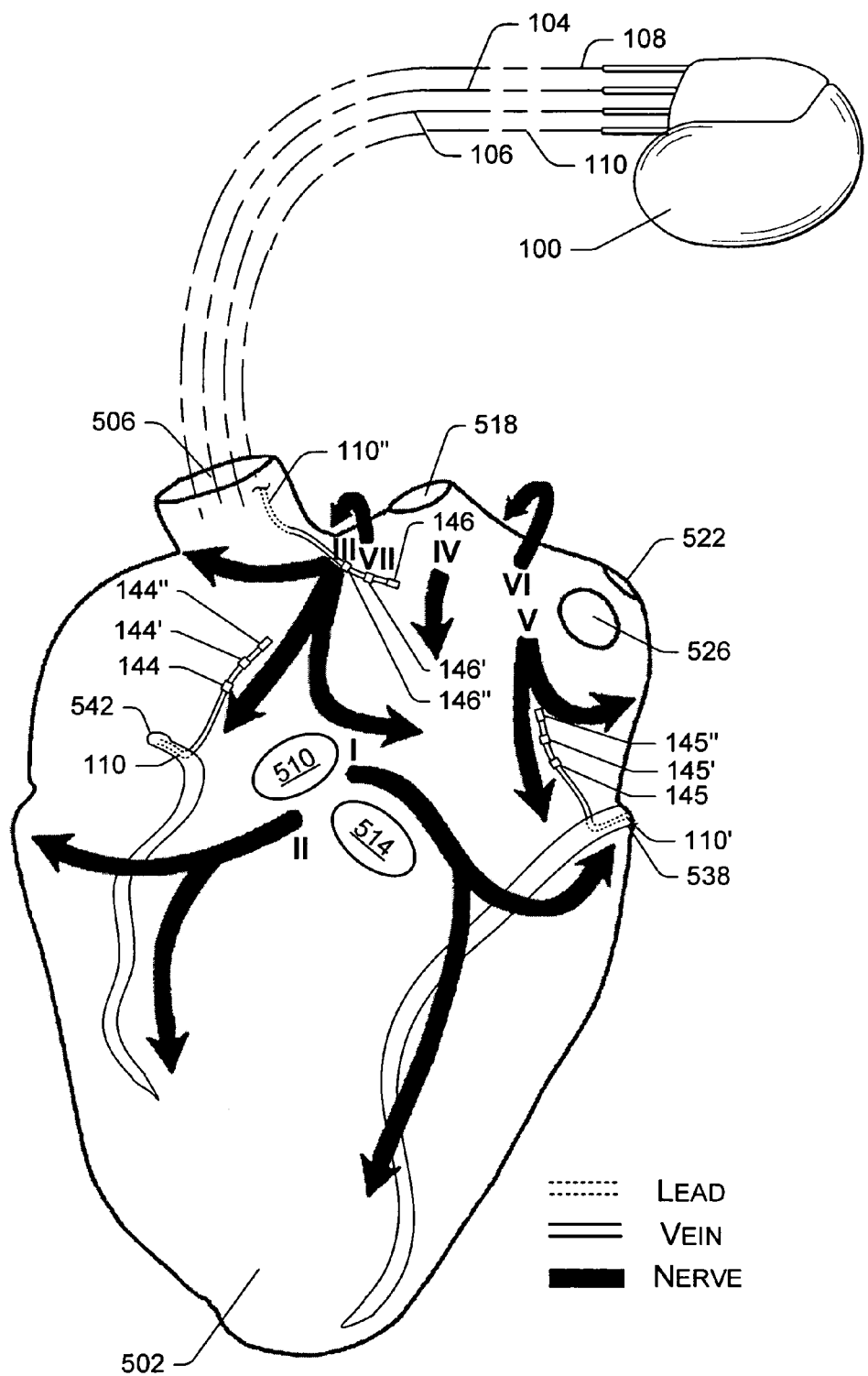
FIG. 6 is an approximate anatomical ventral view diagram of a human heart including some arteries, veins and nerves along with an exemplary stimulation device and exemplary leads.
Figure 7:
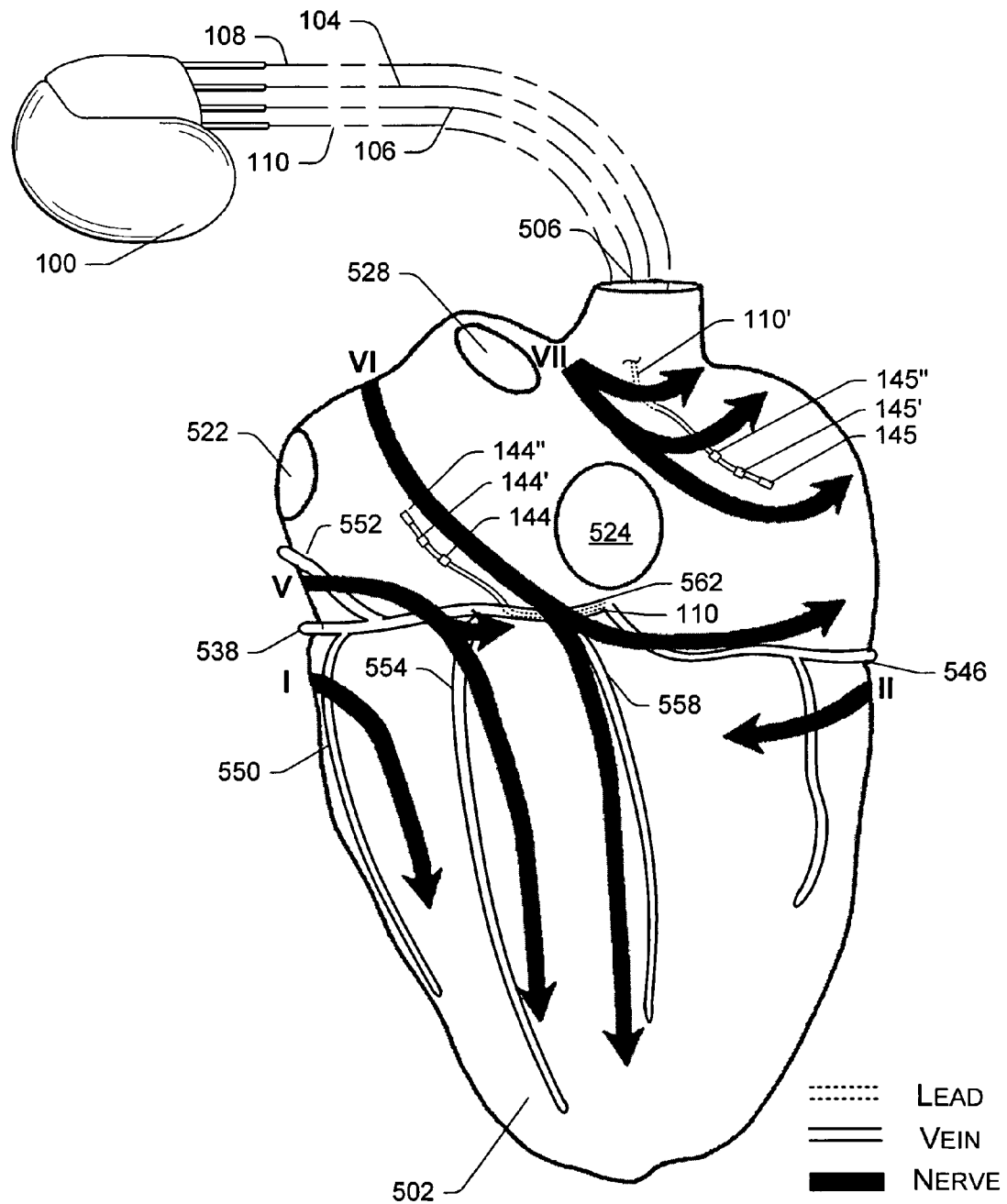
FIG. 7 is an approximate anatomical dorsal view diagram of a human heart including some arteries, veins and nerves along with an exemplary stimulation device and exemplary leads.

Referring to FIGS. 6 and 7, ventral and dorsal views of the heart are shown that correspond to the hearts in FIGS. 4 and 5, respectively. In FIGS. 6 and 7, exemplary leads having exemplary electrodes are also shown in exemplary epicardial locations. For example, FIG. 6 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 6, one exemplary lead 110 has an electrode portion having three electrodes 144, 144', 144". The electrode portion of the lead 110 passes through the wall of the anterior cardiac vein 542 and extends along nerves emanating from the VRA (III) subplexus. Having an electrode portion of a lead positioned as such, activation of at least one of the electrodes 144, 144', 144" may stimulate nerves to affect operation of the SA node. In a similar manner, another exemplary lead 110' has an electrode portion having three electrodes 145, 145', 145". The electrode portion of the lead 110' passes through the wall of the great cardiac vein 538 and extends along nerves emanating from the LD (V) subplexus. Having an electrode portion of a lead positioned as such, activation of at least one of the electrodes 145, 145', 145" may stimulate nerves to affect operation of the AV node. Yet another exemplary lead 110" has an electrode portion having three electrodes 146, 146', 146". The electrode portion of the lead 110" passes through the wall of the superior vena cava (see, e.g., opening of superior vena cava labeled 506) and extends to the VRA (III) subplexus and/or DRA (VII) subplexus. Having an electrode portion of a lead positioned as such, activation of at least one of the electrodes 146, 146', 146" may stimulate nerves to affect operation of the SA node. Of course, the locations and functions of the three leads 110, 110', 110" are only exemplary as a variety of other arrangements are possible. In general, leads may extend to preganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference.

FIG. 7 shows the exemplary stimulation device 100 of FIG. 1 having four leads 104, 106, 108, 110. The leads 104, 106, 108, 110 optionally include branches or bifurcations. In this example, any of the leads may carry electrodes suitable for stimulation of autonomic nerves. As shown in FIG. 7, one exemplary lead 110 has an electrode portion having three electrodes 144, 144', 144". The electrode portion of the lead 110 passes through the wall of the coronary sinus 562 and extends along nerves emanating from the MD (VI) subplexus and/or LD (V) subplexus. Having an electrode portion of a lead positioned as such, activation of at least one of the electrodes 144, 144', 144" may stimulate nerves to affect operation of the AV node. In a similar manner, another exemplary lead 110' has an electrode portion having three electrodes 145, 145', 145". The electrode portion of the lead 110' passes through the wall of the superior vena cava (see, e.g., opening of superior vena cava labeled 506) and extends to the DRA (VII) subplexus and/or to nerves emanating from the DRA (VII) subplexus. Having an electrode portion of a lead positioned as such, activation of at least one of the electrodes 145, 145', 145" may stimulate nerves to affect operation of the SA node. Of course, the locations and functions of the two leads 110, 110' are only exemplary as a variety of other arrangements are possible. In general, leads may extend to pre-ganglionated field regions, ganglionated field regions and/or post-ganglionated field regions. More specifically, leads optionally extend to pre-ganglionated field regions, ganglionated field regions and/or post-ganglionated field regions associated with at least one of the seven subplexus identified in the Pauza et al. reference.

Exemplary Electrode Portion

Figure 8:
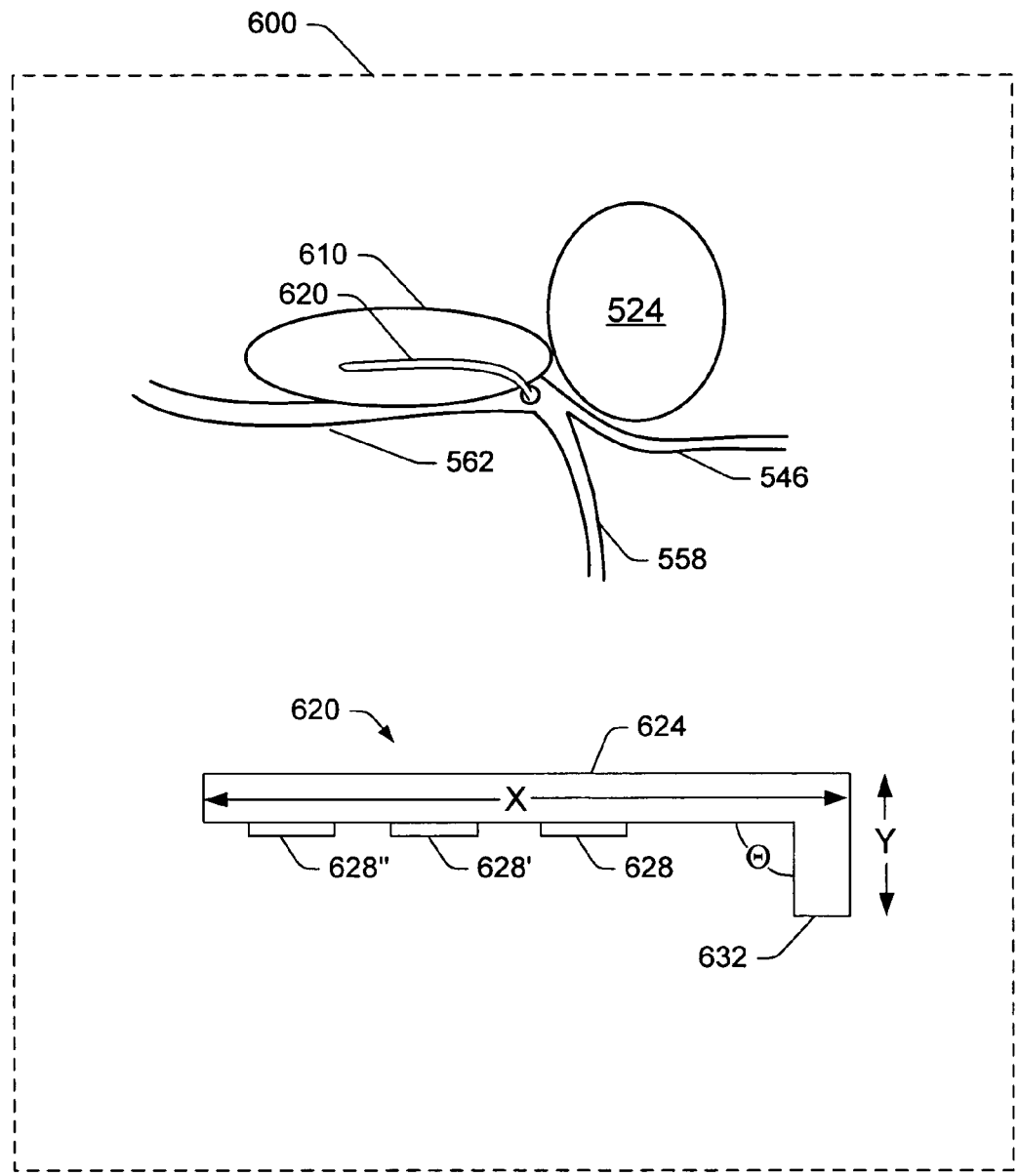
FIG. 8 is an approximate anatomical dorsal view diagram of a "fat pad" located near the inferior vena cava along with an exemplary lead having an electrode portion positioned in and/or proximate to the "fat pad." A more detailed diagram of an exemplary electrode portion is also shown.

FIG. 8. shows an exemplary system 600 for stimulating autonomic nerves in and/or near a fat pad 610. According to this exemplary system, a lead having an electrode portion 620 passes through a wall of the coronary sinus 562. The electrode portion 620 is then positioned on and/or in a dorsal fat pad 610. The dorsal fat pad shown in FIG. 8 optionally includes autonomic nerves, such as, but not limited to, autonomic nerves emanating from a subplexus or subplexuses. For example, a fat pad may include and/or be located proximate to autonomic nerves from the MD (VI) and/or LD (V) subplexuses. Further stimulation of such nerves from an electrode portion (e.g., the electrode portion 620) located at and/or near a fat pad (e.g., the fat pad 610) may optionally allow for control of AV node operation.

A more detailed diagram of an exemplary electrode portion 620 also appears in FIG. 8. This exemplary electrode portion 620 optionally includes a plurality of electrodes, e.g., 628, 628', 628". As shown the electrode portion 620 includes a back portion 624, having a dimension "X", and a header portion 632, having a dimension "Y". Note that the back portion 624 and the header portion 632 also form an angle "Θ", which, as shown, is approximately 90 degrees. For such a header portion, the angle "Θ" typically lies within a range of approximately 30 degrees to approximately 120 degrees and more particularly from approximately 45 degrees to approximately 90 degrees. The back portion 624 optionally includes an insulator such that any charge emanating from an electrode (e.g., the electrodes 628, 628', 628") does not emanate in an undesirable direction. The header portion 632 attaches to a lead and/or is contiguous and/or integral with a lead. In general, positioning of the exemplary electrode portion 620 involves puncturing the wall of a vein, venous structure and/or cardiac chamber.

Figure 9:
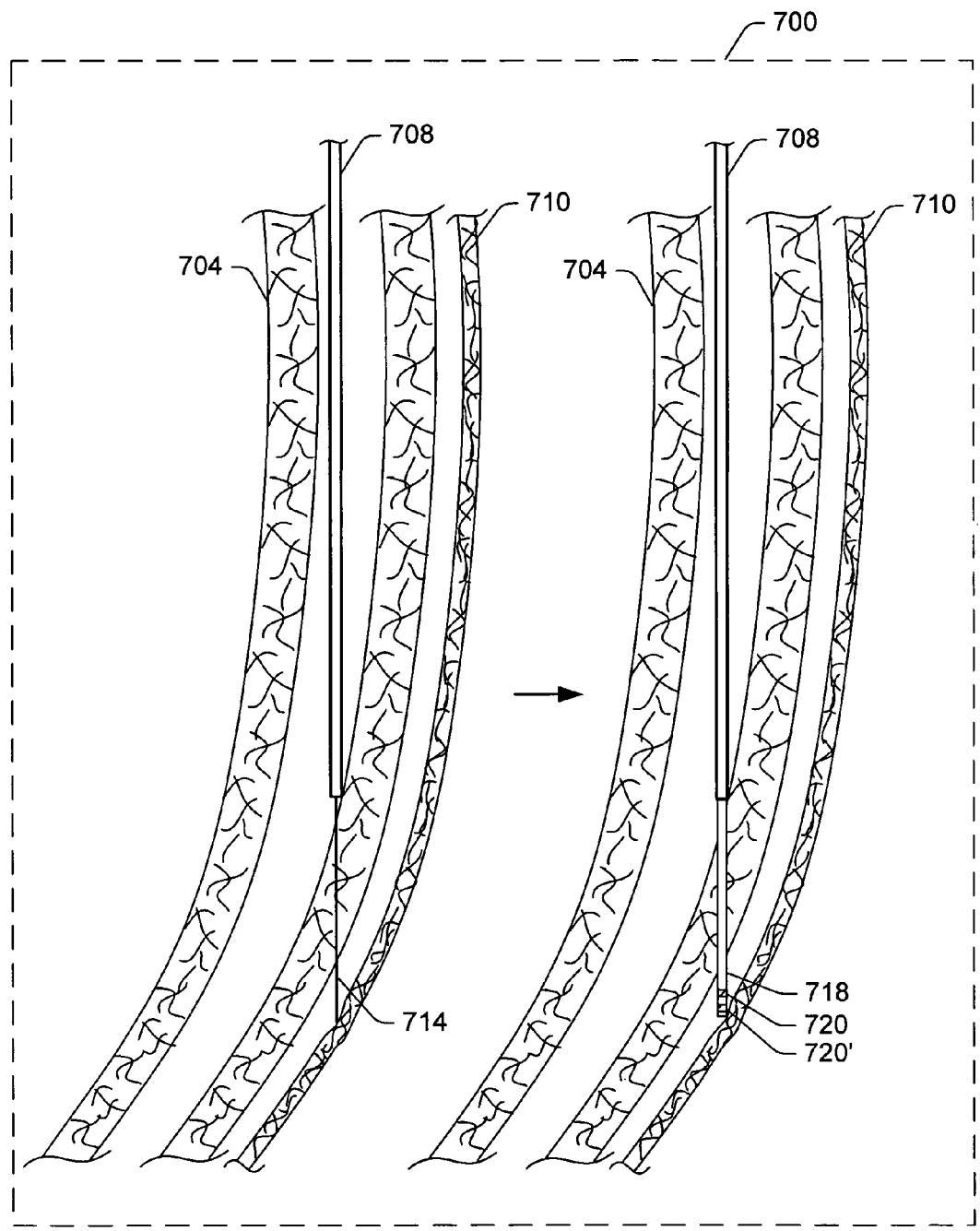
FIG. 9 is an approximate anatomical diagram of an exemplary method for deploying an exemplary electrode portion.
Figure 10:
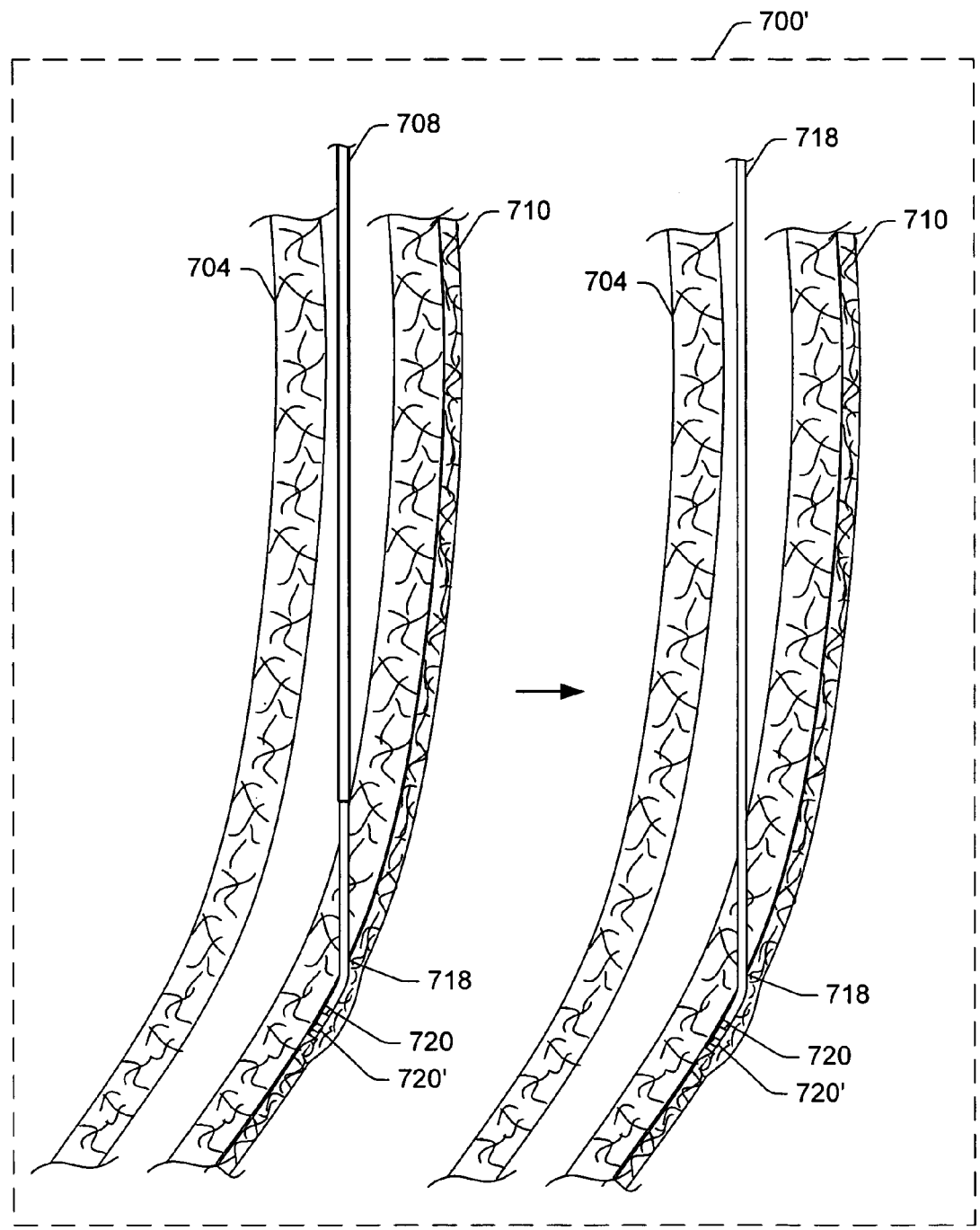
FIG. 10 is an approximate anatomical diagram of an exemplary method for deploying an exemplary electrode portion.

Referring to FIGS. 9 and 10, diagrams illustrating an exemplary method 700, 700' for deploying an electrode portion of a lead is shown. The diagrams of FIGS. 9 and 10 illustrate approximate anatomic features including a cross-section of a cardiac vein 704 and a thin membranous layer 710 known as the pericardium. While a cardiac vein 704 is shown, the exemplary method also applies to penetration of a chamber, such as, but not limited to, the right atrium, which is also surrounded, at least partially, by the pericardium 710. The pericardium is often referred to as a sac-like covering of the heart and, as described herein, can aide in epicardial positioning of leads and/or electrodes. For example, the pericardium can bias a lead and/or an electrode portion of a lead against an epicardial surface. In this example, the epicardial surface may include a fat pad, a vein, venous structure, an artery, myocardium, etc. Further, leads are optionally constructed from material having sufficient pliability. For example, a lead may include a wire, typically used for pacing and having a diameter of approximately 0.5 mm to approximately 1.5 mm. Such a wire is navigable on the epicardial surface and confinable to the epicardial surface by the pericardium. In an exemplary trial, wire having a diameter of approximately 0.8 mm was positioned on the epicardial surface. In addition, use of such sufficiently pliable wire (with appropriate coating and/or electrodes, as needed), in conjunction with a pacing device, allows for delivery of pacing pulses to a variety of sites on the epicardial surface. Further, such wire (with appropriate coating and/or electrodes, as needed), and/or structural equivalents thereof, are suitable for epicardial positioning of leads and/or electrode portions and/or for delivery of pulses aimed at autonomic nerve stimulation. Of course, the use of less pliable wire, leads, and/or electrode portions is also possible. For example, refer to the exemplary lead and electrode portion illustrated in the diagrams of FIG. 8. Resilient wire and/or coatings may aide in positioning and/or urging an electrode against a particular epicardial tissue region and/or penetrating a particular epicardial tissue region, e.g., myocardium, a fat pad, a plexus (including subplexuses), etc.

Referring again to FIGS. 9 and 10, a catheter 708 is positioned within the lumen of the cardiac vein 704. The catheter 708 can aide in guiding and/or positioning of a lead having one or more electrodes. The catheter 708 has one or more lumina, one of which includes a wire 714. According to this exemplary method, the wire 714 penetrates the wall of the cardiac vein 704. Further, the wire 714 upon contacting the pericardium 710 may cause the pericardium to some degree pull away from the epicardial surface and/or deform without rupturing or puncturing. For example, as shown, the wire 714 contacts the pericardium 710 and causes the pericardium 710 to draw away from the epicardial surface, e.g., to draw away from the outer surface of the cardiac vein 704 in a region proximate to the point of contact between the pericardium 710 and the wire 714.

According to the exemplary method 700, once the wire 714 has been positioned, then a lead 718 is advanced along the wire 714. The lead 718 may advance to the end of the wire 714 or to an intermediate point. As shown in FIG. 9, the lead 718 is advanced to the end of the wire 714 to a point in contact with the pericardium 710. As shown, the lead 718 includes two electrodes 720, 720', which are positioned external to the lumen of the cardiac vein 704. Of course, in an alternative arrangement, one or more electrodes are positioned within the cardiac vein 704 and one or more electrodes are positioned external to the lumen of the cardiac vein 704.

Referring to FIG. 10, a continuation of the exemplary method 700 is shown as exemplary method 700'. In progressing from the exemplary method 700 to exemplary method 700', the wire 714 is withdrawn from the electrode portion of the lead 718 and optionally from the entire catheter. According to various exemplary methods and/or devices, such a wire (e.g., 714) is optionally used for positioning only and not for carrying an electrical signal. As shown in FIG. 10, once the wire 714 is withdrawn, the portion of the lead 718 extending beyond the lumen of the cardiac vein 704 conforms to the surface of the cardiac vein 704 (or optionally other epicardial surface). In addition, the pericardium 710 biases the lead 718 against the epicardial surface. Finally, the catheter 708 is retracted while leaving the lead 718 positioned on the epicardial surface.

According to the exemplary method 700, 700', fluoroscopy, MRI or other techniques may aide in positioned. Positioning may also rely on the use of anatomical references, electrical sensing and/or delivery of electrical signals and measured or noted responses thereto.

While the exemplary lead 718 includes two ring electrodes, use of other types of electrodes and/or electrode portions is possible. For example, an exemplary lead optionally includes, but is not limited to, an umbrella, a balloon, and/or other deployable electrode portion. Also note that after deployment, the electrode portion may optionally act as a "stop" to prevent undesirable reentry of the electrode portion to the lumen or chamber.

Exemplary Method for Affecting Cardiac Operation via Autonomic Stimulus

Figure 11:
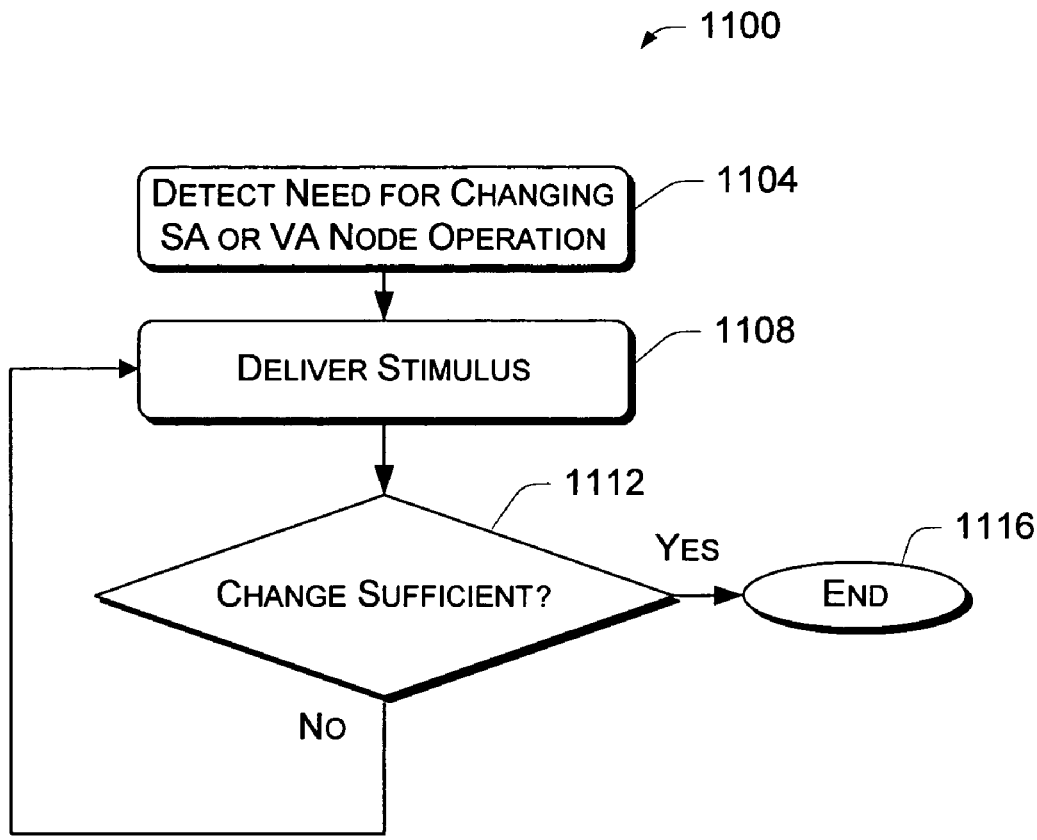
FIG. 11 is a block diagram of an exemplary method for stimulating autonomic nerves to affect operation of an AV node and/or a SA node.

FIG. 11 shows a block diagram of an exemplary method for stimulating autonomic nerves 1100 to affect cardiac operation. In a detection block 1104, a stimulation or other device determines a need for altering cardiac operation. If a need exists, then, in a delivery block 1108, a stimulation device delivers a stimulus to an autonomic nerve. The stimulus may be delivered via a lead that passes through the wall of a vein, venous structure and/or cardiac chamber. The stimulation device optionally delivers the pulses during a refractory period to avoid direct electrical stimulation of the myocardium. In a post-stimulation block 1112, the stimulation or other device determines whether and/or to what extent cardiac operation has changed. If the change is sufficient, then the method 1100 terminates in an end block 1116. If the change is insufficient, then the method 1100 returns to the delivery block 1108. The device is further optionally programmable to make attempts at increasing and/or decreasing the pulse frequency, pulse width, pulse amplitude, and/or other parameters. The method 1100 optionally includes a wait block between the delivery block 1108 and the post-stimulation block 1112 and/or between the post-stimulation block 1112 and the return to the delivery block 1108, in the case that the effect of the stimulation is insufficient. The exemplary method 1100 may also account for other cardiac functions. For example, an exemplary may optionally stimulate post ganglionic autonomic nerves to modulate contractility and/or cardiac output in general. More specifically, such an exemplary method may aim to selectively stimulate sympathetic nerves or autonomic nerves. Further, such an exemplary method may aim to stimulate right sympathetic nerves, left sympathetic nerves, right vagal nerves, and/or left vagal nerves. Such selective stimulation may occur through use of particular pulse parameters and/or epicardial positioning.

Exemplary Method for Affecting Cardiac Operation via Myocardial Stimulus

Figure 12:
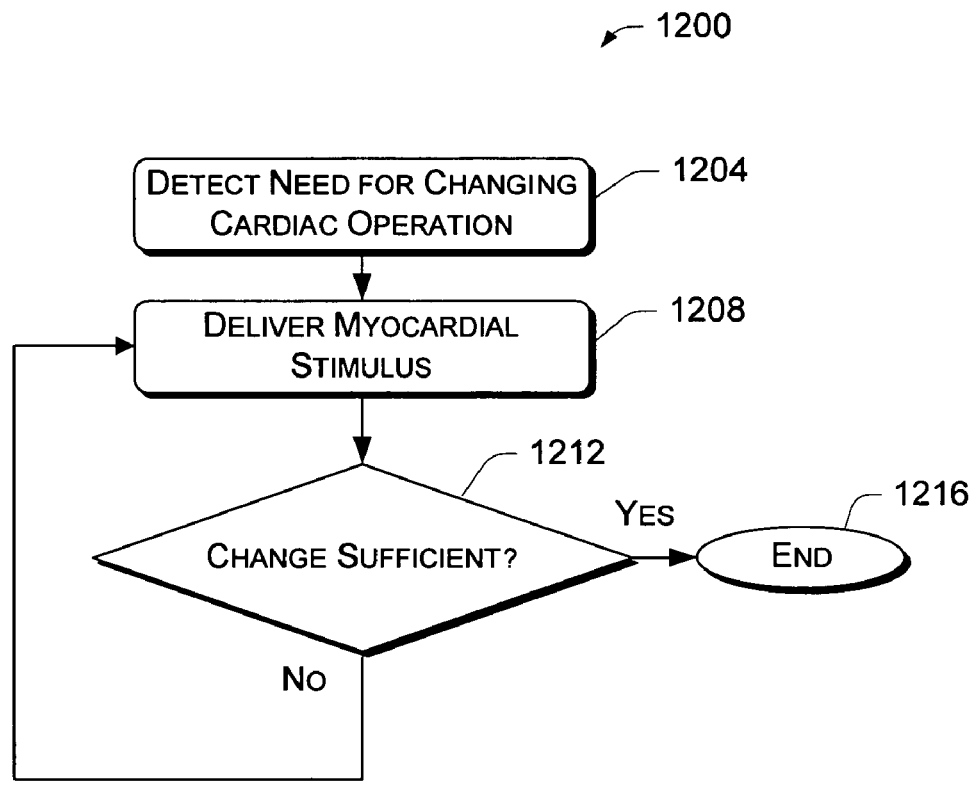
FIG. 12 is a block diagram of an exemplary method for stimulating a tissue region from an epicardial position.

FIG. 12 shows a block diagram of an exemplary method for stimulating the myocardium 1200 to affect cardiac operation. In a detection block 1204, a stimulation or other device determines a need for altering cardiac operation. If a need exists, then, in a delivery block 1208, a stimulation device delivers a stimulus to the myocardium via an electrode positioned epicardially proximate to a myocardial tissue region. The stimulus may be delivered via a lead that passes through the wall of a vein, venous structure and/or cardiac chamber. In a post-stimulation block 1212, the stimulation or other device determines whether and/or to what extent cardiac operation has changed. If the change is sufficient, then the method 1200 terminates in an end block 1216. If the change is insufficient, then the method 1200 returns to the delivery block 1208. The device is further optionally programmable to make attempts at increasing and/or decreasing the pulse frequency, pulse width, pulse amplitude, and/or other parameters. The method 1200 optionally includes a wait block between the delivery block 1208 and the post-stimulation block 1212 and/or between the post-stimulation block 1212 and the return to the delivery block 1208, in the case that the effect of the stimulation is insufficient. The exemplary method 1200 may also account for other cardiac functions.

According to such an exemplary method, at least one epicardially positioned electrode is used to stimulate a patient's left ventricle, right ventricle, right atrium and/or left atrium. For example, in some instances, complications arise, which may hinder placement of a lead into a patient's left ventricle. In such instances, epicardial placement of a lead can allow for stimulation of myocardial tissue of the patient's left ventricle. Further, in this alternative, such a lead is positionable at any of a variety of epicardial sites.

In another variant of this exemplary method, at least one epicardially positioned electrode is used for antitachycardia pacing. For example, electrical pulses delivered via at least one epicardially positioned electrode proximate to one of a patient's atria may terminate atrial fibrillation and/or atrial flutter. Conventional pacing is typically limited to stimulation of a patient's right atrium; however, according to this exemplary method, epicardial stimulation of either or both atria is possible. With respect to the left atrium, access is, for example, possible via a patient's coronary sinus. In general, various exemplary methods and/or exemplary devices allow for positioning of electrodes at a multitude of epicardial sites proximate to atrial tissue, which, in turn, can eliminate a need for high energy, painful atrial defibrillation shocks and hence revolutionize atrial therapy.

Regarding ventricular tachycardia and ventricular fibrillation, various exemplary methods and/or exemplary devices can allow for more effective treatment. For example, in anti-tachycardia pacing, the ability to use of more than one pacing site can allow for more effective treatment of tachyarrhythmias. In this example, a scheme may use one or more epicardial sites in conjunction with endocardial sites. Alternatively, a scheme may use solely a plurality of epicardial sites. Further, according to yet another variant of the exemplary method, ventricular tachycardia and/or ventricular fibrillation are treated using one or more epicardial shocking coil electrodes positioned, for example, over the left ventricle and used either alone or in conjunction with right ventricular endocardial or even epicardial electrodes.

Exemplary Method for Affecting Cardiac Operation

Figure 13:
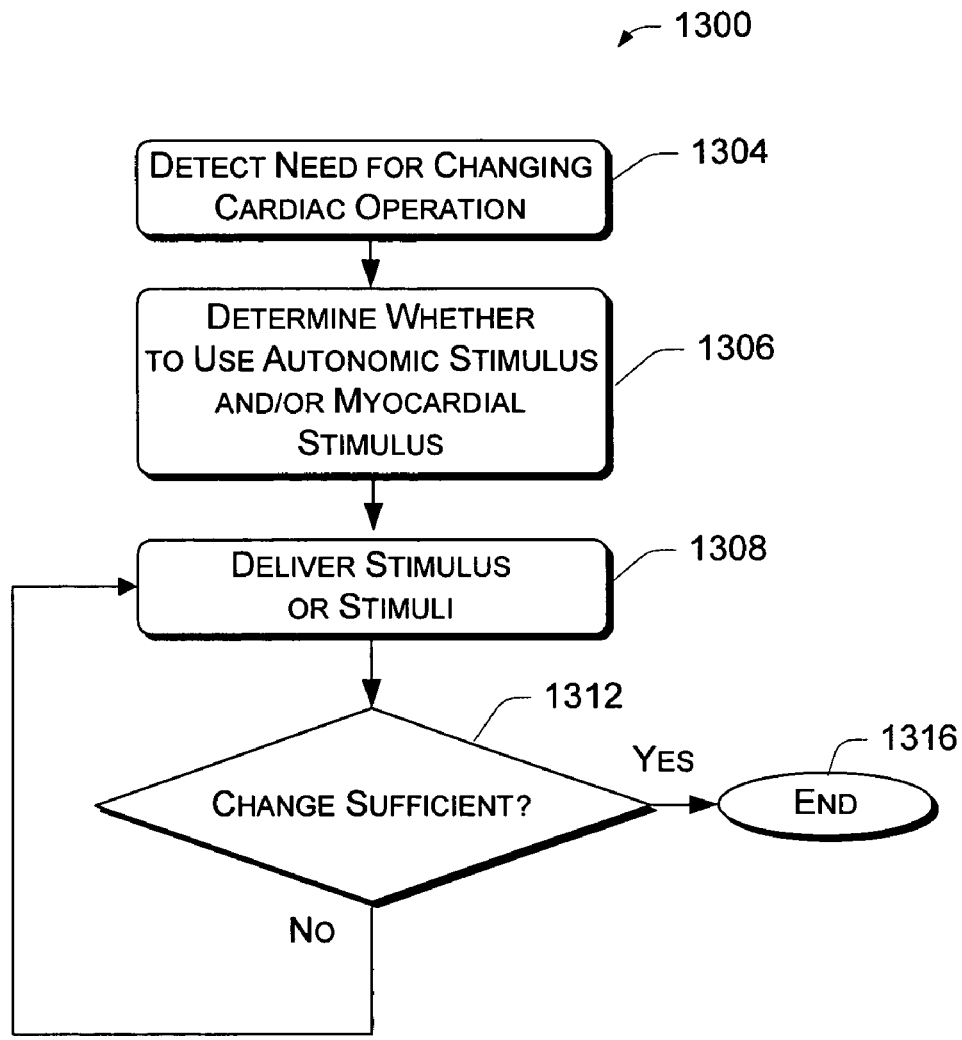
FIG. 13 is a block diagram of an exemplary method for stimulating a tissue region from an epicardial position.

FIG. 13 shows a block diagram of an exemplary method for stimulating autonomic nerves and/or myocardial tissue 1300 to affect cardiac operation. In a detection block 1304, a stimulation or other device determines a need for altering cardiac operation. If a need exists, then, in a determination block 1306, the stimulation device (or other device) determines whether to stimulate an autonomic nerve and/or to stimulate myocardial tissue. Then, in a delivery block 1308, the stimulation device delivers a stimulus to an autonomic nerve and/or to myocardial tissue. The stimulus may be delivered via at least one lead that passes through the wall of a vein, venous structure and/or cardiac chamber. The stimulation device optionally delivers autonomic nerve pulses during a refractory period to avoid direct electrical stimulation of the myocardium. In a post-stimulation block 1312, the stimulation or other device determines whether and/or to what extent cardiac operation has changed. If the change is sufficient, then the method 1300 terminates in an end block 1316. If the change is insufficient, then the method 1300 returns to the determination block 1306 or the delivery block 1308. The device is further optionally programmable to make attempts at increasing and/or decreasing the pulse frequency, pulse width, pulse amplitude, and/or other parameters. The method 1300 optionally includes a wait block between the delivery block 1108 and the post-stimulation block 1312 and/or between the post-stimulation block 1312 and the return to the delivery block 1308, in the case that the effect of the stimulation is insufficient. The exemplary method 1300 may also account for other cardiac functions.

Selecting and/or Positioning Leads and/or Electrodes

An exemplary method for selecting and/or positioning a lead and/or an electrode is optionally implemented during implantation and/or after implantation. For example, during an implantation procedure, a patient is optionally instrumented to monitor heart function. For example, heart rate may be monitored via an EKG and contractility via arterial pressure sensors (e.g., the time derivative of the pressure can provide a good measure of contractility). In this example, monitoring of cardiac function and/or other functions may occur through use of external instrumentation and/or through use of implanted leads and/or sensors.

Consider a situation wherein parasympathetic tuning via parasympathetic nerve stimulation aims to decrease heart rate. In such a situation, an exemplary method includes adjusting pulse amplitude and/or pulse frequency to relatively high values, automatically or manually (e.g., an implantable device having a lead and/or electrode implantation, selection and/or positioning mode(s)). In this exemplary method, through use of stimulation pulses and monitoring of cardiac function and/or other functions, a lead and/or electrode is positioned during implantation to achieve an optimal and/or a satisfactory decrease in heart rate (e.g., an increase of therapeutic value). In this exemplary method, for example, a physician may slowly move a lead throughout an appropriate region and deliver pulses until a desired decrease in heart rate is seen maximally via monitoring.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A method for changing cardiac operation comprising:
    passing a lead through a wall of an epicardial vein or an epicardial venous structure wherein the lead includes an electrode portion;
    positioning the electrode portion proximate to an epicardial autonomic nerve; and
    delivering an electrical signal to the electrode portion to stimulate the epicardial autonomic nerve and thereby change cardiac operation;
    wherein the positioning includes positioning the electrode portion proximate to an autonomic nerve in a subplexus.

2. The method of claim 1, wherein the electrode portion is a deployable electrode portion and the method further comprises deploying the deployable electrode portion.

3. The method of claim 1, wherein the subplexus is the dorsal right atrial ganglionated subplexus and the delivering changes operation of the SA node.

4. The method of claim 1, wherein the subplexus is the ventral right atrial ganglionated subplexus and the delivering changes operation of the SA node.

5. The method of claim 1, wherein the subplexus is the middle dorsal ganglionated subplexus and the delivering changes operation of the AV node.

6. The method of claim 1, wherein the subplexus is the left dorsal ganglionated subplexus and the delivering changes operation of the AV node.

7. The method of claim 1, wherein the electrical signal includes parameters, the parameters selected from the group consisting of amplitude, frequency, voltage, current, energy, charge, power, and pulse width.

8. A method for changing cardiac operation comprising:
    passing a lead through a wall of an epicardial vein or an epicardial venous structure wherein the lead includes an electrode portion;
    positioning the electrode portion proximate to an epicardial autonomic nerve; and
    delivering an electrical signal to the electrode portion to stimulate the epicardial autonomic nerve and thereby change cardiac operation;
    wherein the positioning includes positioning the electrode portion proximate to a fat pad; and
    wherein the fat pad is a dorsal fat pad located proximate to the inferior vena cava.

9. A method for changing cardiac operation comprising:
    passing a lead through a wall of an epicardial vein or an epicardial venous structure wherein the lead includes an electrode portion;
    positioning the electrode portion proximate to an epicardial autonomic nerve; and
    delivering an electrical signal to the electrode portion to stimulate the epicardial autonomic nerve and thereby change cardiac operation;
    wherein the positioning includes positioning the electrode portion proximate to a fat pad; and
    wherein the delivering changes operation of the AV node.

* * * * *

UNITED STATES PATENT AND TRADEMARK OFFICE
CERTIFICATE OF CORRECTION

PATENT NO. : 7,653,440 B1
APPLICATION NO. : 11/172755
DATED : January 26, 2010
INVENTOR(S) : Bornzin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1104 days.

Signed and Sealed this

Twenty-third Day of November, 2010

David J. Kappos
*Director of the United States Patent and Trademark Office*